Figure 1:
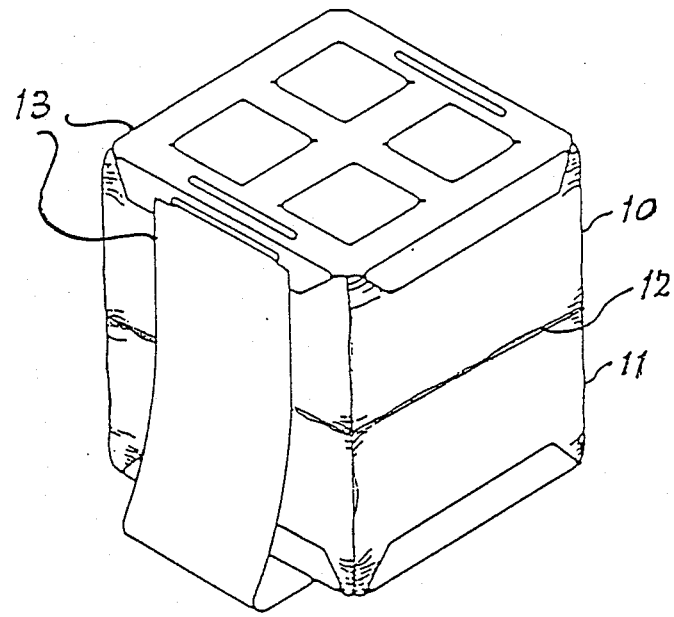

United States Patent [19]

Hambleton

[11] Patent Number: 4,902,478
[45] Date of Patent: Feb. 20, 1990

[54] INDICATOR SHEET FOR AN AUTOCLAVE TEST PACK

[75] Inventor: Roger Hambleton, Stockport, England

[73] Assignee: The Victoria University of Manchester, Manchester, England

[21] Appl. No.: 235,897

[22] PCT Filed: Feb. 20, 1987

[86] PCT No.: PCT/GB87/00125
§ 371 Date: Sep. 7, 1988
§ 102(e) Date: Sep. 7, 1988

[87] PCT Pub. No.: WO87/04931
PCT Pub. Date: Aug. 27, 1987

[30] Foreign Application Priority Data

Feb. 22, 1986 [GB] United Kingdom ............... 8604463
May 27, 1986 [GB] United Kingdom ............... 8612775

[51] Int. Cl.[4] .......................................... G01N 31/00
[52] U.S. Cl. ......................................... 422/56; 422/57; 422/61; 422/86; 422/87; 422/88; 422/158; 436/1; 435/31; 206/438; 206/439
[58] Field of Search ................................. 422/55–57, 422/61, 86–88, 158; 436/1; 435/31; 206/438, 439

[56] References Cited

U.S. PATENT DOCUMENTS

| | | | |
|---|---|---|---|
| 4,382,063 | 5/1983 | Romito et al. | 422/58 X |
| 4,576,795 | 3/1986 | Bruso | 422/61 X |
| 4,579,715 | 4/1986 | Bruso | 422/58 |
| 4,596,696 | 6/1986 | Scoville, Jr. | 422/61 |
| 4,692,307 | 9/1987 | Bruso | 422/61 X |
| 4,699,765 | 10/1987 | Hambleton | 422/61 X |

FOREIGN PATENT DOCUMENTS 8704931 8/1987 World Int. Prop. O. .......... 422/292

Primary Examiner—Barry S. Richman
Assistant Examiner—Lynn M. Kummert
Attorney, Agent, or Firm—Nies, Webner, Kurz & Bergert

[57] ABSTRACT

An indicator sheet for an autoclave test pack wherein a pair of porous masses (10) are held in close superimposed relationship by means of a clamp (13) with the indicator sheet (12) sandwiched between them. The indicator sheet (12) has printed thereon a pattern of markings (14) formed from one or more substances which are adapted under steam sterilizing conditions to provide an indication of the presence of air and/or excessive moisture such that each is evident and individually identifiable.

9 Claims, 1 Drawing Sheet

U.S. Patent    Feb. 20, 1990    4,902,478

INDICATOR SHEET FOR AN AUTOCLAVE TEST PACK

This invention concerns a device for testing the efficiency of autoclaves such as those used in hospitals for sterilizing porous loads, and for detecting the presence of air in such a system, and is particularly concerned with an indicator sheet for use in such a device, which provides a visual indication of the presence of air and/or other substances under steam sterilizing conditions.

Porous loads are sterilized by subjecting them to saturated steam at a temperature of between 134° C. and 138° C. for a period of not less than 3 minutes. In order to ensure correct sterilizing conditions, the steam must penetrate unhindered to all parts of the load. This can be achieved only if all of the air is first removed from the sterilizer vessel and from its load, which is accomplished typically by a process of evacuation and steam flushing of the sterilizing vessel and its load.

Failure to remove all of the air or the subsequent leakage of air into an evacuated chamber, or the introduction of air or other gases in the steam supply, can cause gas pockets to remain within the porous load, usually in the inner regions thereof. In this case, the temperature within some parts of the load might be lower than that required during all or part of the sterilizing process. Many types of testing device are known for this purpose including the so-called Bowie Dick towel test utilising a pack of linen Huckaback towels measuring some 270 mm high and about 300 mm × 200 mm in plan. Another known system utilises sheets of porous paper or card, and in all of these cases it is necessary for an indicator to be placed in the centre of the stack so that after the test the indicator may be inspected to detect any parts thereof where air might have been present.

The test pack is processed in the sterilizer and the satisfactory result would show an even change in appearance across the whole of the indicator sheet, whereas the presence of air in the stack is indicated by a failure of the indicator to change its appearance in certain areas, usually at the centre. The test must be carried out daily before the sterilizer is used for the production of sterile porous loads.

Such indicators conventionally may consist of so-called autoclave tape which is placed across a sheet of paper, and reacts visibly to the presence of air and moisture under steam sterilizing conditions. Alternatively, there are available certain manufactured sheets having an indicator pattern printed thereon from a substance which, again, reacts by changing its appearance under steam sterilizing conditions.

It has been found that these conventional types of indicator suffer from the disadvantage that their appearance is affected by the presence of excessive moisture during the test, and this can lead to a false reading when attempting to detect the presence of air. In some cases, this can have the effect of a substance from the tape or sheet being transferred onto the material of the pack which in turn further affects the appearance of the indicator producing still further misleading results.

One kind of device for detecting the presence of air in a steam sterilizer has been proposed and comprises a first porous mass of at least substantially man-made material, a second porous mass of a similar material, an indicator adapted to undergo a visual change under moist heat sterilizing conditions and sandwiched between the masses thus to be in intimate contact therewith, and means for removably holding the masses and indicator in close superimposed relationship, said means being permeable to allow the free passage of air and steam to the external surfaces of the porous masses.

In this kind of device where a man-made material such as polypropylene is used in place of linen or paper, the presence of excessive moisture in the applied steam is particularly detrimental since none of the moisture can be absorbed by the pack. As a result, the affect of the moisture on the indicator is more pronounced, and it is an object of the present invention to provide an improved indicator for use, particularly though not exclusively, with an autoclave test pack incorporating man-made materials.

According to the present invention there is provided an indicator sheet for an autoclave test pack, the sheet bearing on at least one of its faces, a pattern of indicator markings which under steam sterilizing conditions, undergo a visual change to indicate the presence of air or of excessive moisture, or both, the markings formed from at least two substances which provide different indications, one being sensitive to air and the other to excessive moisture.

Figure 2:
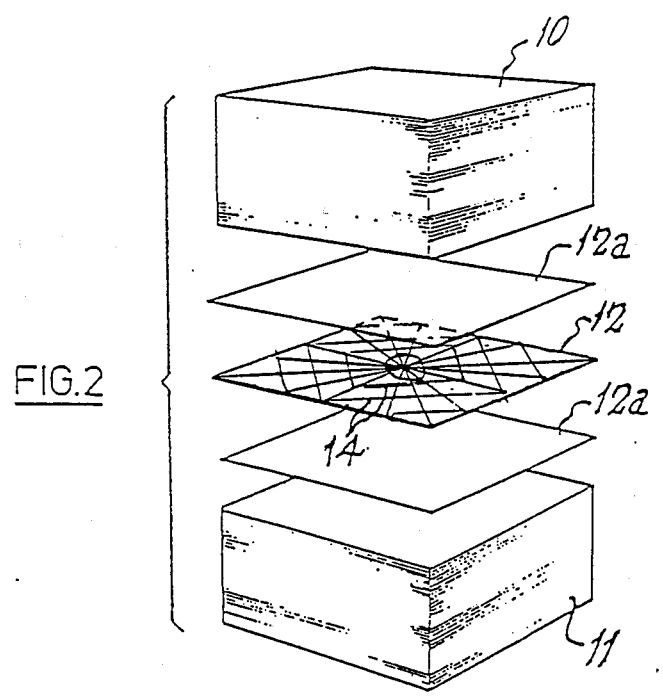

The invention will be further apparent from the following description, given by way of example only, with reference to the accompanying drawings in which:

FIG. 1 is a perspective view of a device made in accordance with the invention; and FIG. 2 is an exploded view of some of the constituent parts thereof.

Referring now to the drawings, one form of device for detecting the presence of air in a steam sterilizer comprises first and second porous masses 10 and 11 each formed from a stack of single sheets of a man-made woven or non-woven material such as spun bonded polypropylene having a weight in the region of 50–150 (and typically in the region of 100) grams per square metre. Each mass contains an appropriate number (typically between 60 and 300) of such sheets arranged in close superimposed relationship. Sandwiched between the masses 10 and 11 is an indicator sheet 12 bearing on at least one of its faces, a pattern of indicator markings 14 adapted to undergo a visual change during a test.

The markings 14 are such that after a test has been carried out to detect the presence of air under steam sterilizing conditions, there will be a clear indication on the sheet 12 of the presence of air and/or excessive entrained moisture in the applied steam. Since excessive moisture can produce a false reading, perhaps suggesting to the operator the presence of air when no air is present, it is necessary to detect the presence of droplets of entrained moisture in the otherwise saturated steam, and for this to be visible on the indicator sheet as distinct from any indication of the presence of air. Thus in accordance with the invention the pattern of indicator markings printed or otherwise placed on the indicator sheet 12 is arranged to extend across the whole surface area of at least one face of the sheet and consists of at least two substances which are capable of providing separately identifiable indications of the presence of air and excessive moisture.

A cover sheet 12a of a porous and absorbent material such as paper may be interposed between each face of indicator sheet 12 and the adjacent surface of the mass 10 or 11. This may take the form of unglazed paper (bond) of weight typically 80g per square metre.

As can be seen in FIG. 1, the masses 10 and 11, and indicator sheet 12 are placed in close superimposed relationship into a closable box or clamp 13 as a close fit therewithin. When closed the clamp applies a slight compressive force to its contents to ensure that they are firmly held together. The clamp may be of stainless steel or plastics, and allows free access of air and steam to the test pack. The pack is constructed in a manner which permits use for a number of successive tests, for example, up to 30 but preferably 10–15.

As can be seen from the drawing, in this embodiment, the pack when assembled is approximately cuboid and it has a side dimension typically in the region of 5–30 cm and preferably about 15 cm to allow for a reduction in height through compression during use.

The material from which the masses 10 and 11 are produced shall not give rise to exothermic reactions when hydrated and must exhibit air/steam penetration characteristics similar to those of Huckaback towels which comply with British Standard BS 1781.

Experimental work has demonstrated that the device as described is capable of detecting the presence of air in a sterilizer. It is also clear from temperature measurements made within the device that the presence of air leads to a depression of temperature at the centre of the test pack similar to that observed with the Huckaback towel pack used in the conventional Bowie/Dick test.

In one example of indicator sheet 12, the markings 14 are formed from two substances printed or otherwise placed on one face of the sheet, or one on each face, which change their appearances differentially, one being sensitive to excessive moisture and the other to air.

A substance which changes its appearance under steam sterilizing conditions is lead carbonate ink which converts to lead oxide and turns from light to dark in the absence of air. If pockets of air are present then these are indicated by zones where the substance has not changed or only partially changed its appearance. This substance, in the presence of excessive moisture under steam sterilizing conditions, will also tend to be solubilised and will thus transfer from the surface of the indicator sheet to the next adjacent surface such as a cover sheet 12a in the example given. Sheet 12a is preferably of an absorbant material such as paper.

In conventional cases where no moisture detection is called for, any tendency for the substance to transfer from one sheet to another would be prevented by coating of the lead carbonate ink with a moisture-impervious substance such as varnish. Thus protected, it is insoluble.

In one specific example as illustrated the indicator sheet 12 has a pattern of radial lines projecting from a central position towards the edges. Each line may be between 0.25 cm and 2 cm in width and printed using a lead carbonate ink. The lines may be of uniform thickness or tapering towards the centre.

Certain selected and appropriately indicated ones of these lines can be protected against transfer in the presence of excessive moisture whilst others are left unprotected. This may be by pre-encapsulation or aftercoating of the ink using a moisture-impervious, for example, polymeric substance.

The shape and arrangement of the lines or other markings across the face of the sheet is to some extent arbitrary but should extend substantially across the entire face so that when subjected to steam sterilizing conditions in a test pack of the kind described above the presence of air would be visible as areas where the ink is unchanged or only partially changed, whilst the presence of excessive moisture would be visible by way of transfer of the unprotected markings in those areas when excessive moisture is present.

Conveniently the sheet may be some 30 cm by 12–15 cm and folded to be approximately square with a side dimension in the region of 12–15 cm so that it can be placed in the test pack with two opposed marked faces.

The indicator sheet upon which the markings are applied is preferably of a porous material such as paper, and in use this may be placed in the pack with cover sheets of similar material super-imposed on both marked faces as illustrated.

For certain applications the marked indicator sheet is preferably enclosed within an envelope of porous material such as spun bonded polypropylene or cellulosic material such as cotton or similar fabrics, or compressed paper or board-like material. In this way, the indicator sheet can be packaged and remain substantially unexposed prior to use.

Substances other than lead carbonate ink may be used provided that they are capable of indicating the presence of air or excessive moisture under steam sterilizing conditions.

In some case it is advantageous to use two substances which give visual indications, for example, by change to different colours. One example might be amino acid compositions containing an indicator which changes from yellow to blue in the absence of air but from yellow to brown in the presence of air. Markings of such a material may be applied to the sheet in conjunction with one or more other materials indicating the presence of excessive moisture.

By providing an indicator sheet which will perform as described above under steam sterilizing conditions, a more positive and clearly identifiable result can be obtained during an autoclave test so that it can be carried out by lesser skilled personnel not trained to recognise, without difficulty, the difference between an indicator affected by the presence of air, and one affected by excessive moisture, with or without the presence of air.

In an alternative form of test pack, incorporating an indicator sheet in accordance with the invention, the porous masses, when assembled, may be other than cuboid presenting, for example, a flatter rectangular pack some 4 cm in height with side dimensions in the regions of 30 cm and 20 cm respectively.

I claim:

1. An indicator sheet for an autoclave test pack, the sheet bearing on at least one of its faces, a pattern of indicator markings which, under steam sterilizing conditions, undergo a visual change to indicate the presence of air or of excessive moisture, or both, the markings being formed from at least two substances which provide different indications, one being sensitive to air and the other to excessive moisture.

2. An indicator sheet according to claim 1, wherein at least one of the substances is lead carbonate ink, the pattern including some markings where the ink is protected and cannot be solubilized while other areas are unprotected such that they become solubilized in the presence of excessive moisture and are transferred onto an adjacent surface.

3. An indicator sheet according to claim 2, wherein the protected markings are formed from pre-encapsulated ink.

4. An indicator sheet according to claim 2, wherein the protected markings are formed from ink coated after application to the sheet.

5. An indicator sheet according to claim 2, wherein the protected markings are formed from ink pre-encapsulated or after-coated with a polymeric material.

6. An indicator sheet according to claim 1, wherein at least one of said substances is an amino acid composition sensitive to the presence of air.

7. An indicator sheet according to any one of claims 1 through 6, in combination with an autoclave test pack comprising a first porous mass of at least substantially manmade material, a second porous mass of at least substantially man-made material, the indicator sheet being sandwiched between the first and second masses thus to be in intimate contact therewith, and means for removably holding the first and second masses and indicator sheet in close superimposed relationship, said means for removably holding being permeable to allow free passage of air and steam to the first and second porous masses.

8. An indicator sheet in combination with an autoclave test pack according to claim 7, wherein each said porous mass is formed from a stack of single sheets of a man-made woven or non-woven material having a weight in the region of 50 to 150 grams per square meter.

9. An indicator sheet in combination with an autoclave test pack according to claim 7, wherein said means for removably holding the masses and indicator sheet in close superimposed relationship is formed as a clamp enclosing the masses and indicator sheet and applying a slight compressive force to hold firmly together the masses and indicator sheet.

* * * * *